United States Patent
Telson et al.

(10) Patent No.: US 8,868,151 B2
(45) Date of Patent: Oct. 21, 2014

(54) ELECTROCHEMICAL IMPEDANCE SPECTROSCOPY ENABLED CONTINUOUS GLUCOSE MONITORING SENSOR SYSTEM

(75) Inventors: Stanley A. Telson, White Plains, NY (US); Raeann Gifford, Cortland Manor, NY (US); Jiangfeng Fei, Sleepy Hollow, NY (US); Jeffery S. Reynolds, New Fairfield, CT (US)

(73) Assignee: Bayer HealthCare LLC, Whippany, NJ (US)

( * ) Notice: Subject to any disclaimer, the term of this patent is extended or adjusted under 35 U.S.C. 154(b) by 702 days.

(21) Appl. No.: 12/857,116

(22) Filed: Aug. 16, 2010

(65) Prior Publication Data

US 2011/0040163 A1    Feb. 17, 2011

Related U.S. Application Data

(60) Provisional application No. 61/274,321, filed on Aug. 14, 2009.

(51) Int. Cl.
  *A61B 5/05* (2006.01)
  *A61B 5/145* (2006.01)
  *A61B 5/053* (2006.01)
(52) U.S. Cl.
  CPC .............. *A61B 5/14532* (2013.01); *A61B 5/053* (2013.01)
  USPC .................. 600/345; 600/347; 422/82.01
(58) Field of Classification Search
  USPC ......................... 600/345, 347, 354
  See application file for complete search history.

(56) References Cited

U.S. PATENT DOCUMENTS

| | | | | |
|---|---|---|---|---|
| 5,126,654 | A * | 6/1992 | Murphy et al. | 324/71.2 |
| 5,396,897 | A * | 3/1995 | Jain et al. | 600/561 |
| 5,846,744 | A | 12/1998 | Athey et al. | |
| 6,088,608 | A | 7/2000 | Schulman et al. | |
| 6,613,379 | B2 | 9/2003 | Ward et al. | |
| 7,488,601 | B2 | 2/2009 | Burke et al. | |
| 2002/0042561 | A1 * | 4/2002 | Schulman et al. | 600/345 |
| 2004/0108226 | A1 | 6/2004 | Polychronakos et al. | |
| 2005/0085743 | A1 * | 4/2005 | Hacker et al. | 600/554 |
| 2009/0027070 | A1 * | 1/2009 | Gelling | 324/693 |
| 2010/0169035 | A1 * | 7/2010 | Liang et al. | 702/65 |

OTHER PUBLICATIONS

Karp et al., IEEE Sensors Journal, 8(1); 104-112 (2008).

* cited by examiner

*Primary Examiner* — Navin Natnithithadha
*Assistant Examiner* — Etsub Berhanu
(74) *Attorney, Agent, or Firm* — Lerner, David, Littenberg, Krumholz & Mentlik, LLP

(57) ABSTRACT

The use of electrical impedance spectroscopy to adjust calibration settings in an in vivo monitoring system, such as an in vivo continuous glucose monitoring sensor. The adjustments can compensate for the condition of the sensor membrane in vivo.

17 Claims, 5 Drawing Sheets

Fig. 1 - Prior Art

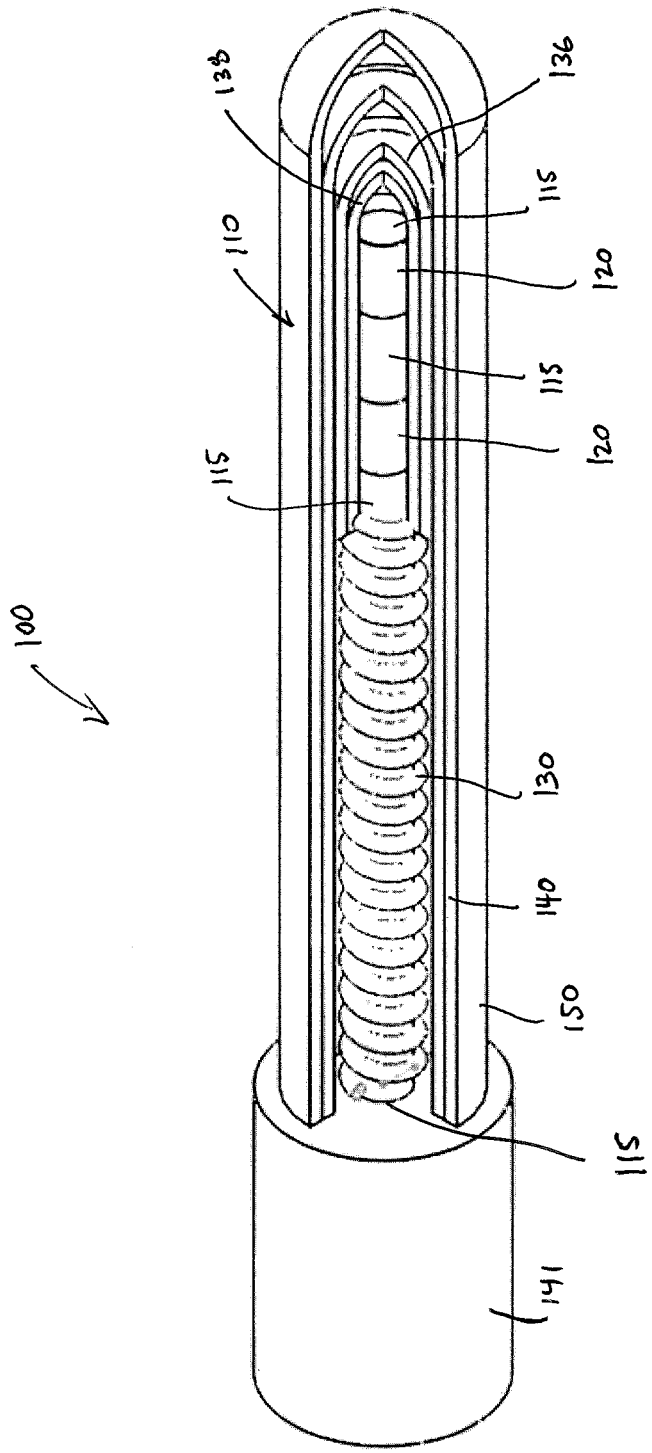

ELECTROCHEMICAL IMPEDANCE SPECTROSCOPY ENABLED CONTINUOUS GLUCOSE MONITORING SENSOR SYSTEM

CROSS-REFERENCE TO RELATED APPLICATIONS

This application claims the benefit of the filing date of U.S. Provisional Patent Application No. 61/274,321 filed Aug. 14, 2009, the disclosure of which is hereby incorporated herein by reference.

BACKGROUND OF THE INVENTION

Diabetes mellitus, often simply referred to as diabetes, is a significant global health concern and is a leading cause of illness and death. This is true even in developed countries, where elevated weight and obesity contributes to certain forms of diabetes. Although various methods of controlling diabetes and its symptoms have been found, there is yet no cure.

Insulin is a hormone produced in the pancreas and is used by the body to convert sugar and other foods into energy. Individuals affected with diabetes either do not produce sufficient insulin or do not respond properly to the insulin they produce. Sugar levels in the body therefore build until the sugar is excreted through urine. Those afflicted with diabetes suffer from various ailments, including ailments affecting the eyes, kidneys, heart, and limbs.

Persons with Type 1 diabetes generally do not produce insulin and represent approximately 5-15% of all cases. Type 1 diabetes was formerly referred to as juvenile-onset diabetes or insulin-dependent diabetes mellitus (IDDM) and almost always requires the person afflicted to take insulin injections. Type 2 diabetes, formerly referred to as adult-onset diabetes or non-insulin-dependent diabetes mellitus (NIDDM), represents the remaining 85-95% of cases and is usually associated with persons over the age of 40. Type 2 diabetes develops slowly as one ages, typically in association with obesity or unhealthy weight gain.

Since the early 1920's, all forms of diabetes have been treatable with insulin. Insulin allows persons with diabetes to live nearly normal lives with virtually no long term affects if administered properly. For those with Type 1 diabetes who have limited or no natural insulin production, therapies typically include routine insulin injections. Those with Type 2 diabetes are typically treated through diet control, weight loss, and exercise, although insulin injections may also be required occasionally.

Individuals with Type 2 diabetes that control their blood-sugar level through diet may test their blood sugar level once per day, generally before breakfast. Persons with Type 1 diabetes and Type 2 diabetes that utilize insulin injections may test more often, typically at least 3 times and as often as times per day. Such testing means typically include piercing of the skin and placing a droplet of blood on a test strip. The test strip may in turn change color to represent a blood-glucose level, or may be associated with a meter that provides a digital representation of the blood-glucose level. In any event, only at the moment of testing does one know their blood glucose level.

Many believe that the future of glucose testing lies in methods that enable continuous blood glucose monitoring (CGM) so as to avoid the need for testing by the patient and to provide a greater level of accuracy in testing, at least by virtue of additional data points. A typical CGM consists of a disposable glucose sensor placed under the skin, a receiver that a user may wear on his/her body much like a pager, and a transmitter adapted to provide communication between the sensor and the meter. Although there are few currently available commercial systems, those that are available typically have sensors that last between 3 and 7 days in vivo. As such, the sensors must be replaced periodically.

CGM sensors typically include a polymer membrane that may be damaged or otherwise compromised during insertion. Yet, it is presently difficult to assess sensor viability after insertion. Even if not damaged during insertion, the membrane may incur biofouling through biological reaction within the body, such as through protein absorption, which adversely affects performance of the sensor.

Another issue with sensors that is difficult to currently assess is the level of movement of the sensor once inserted. Such movement is typically referred to as pistoning, and is preferably avoided for most accurate readings as the movement causes inconsistent readings.

It would therefore be advantageous to provide a sensor system and method for determining the viability of a sensor in vivo. It would be most preferred if a calibration profile of the sensor could be adjusted in response to changing conditions in vivo.

BRIEF SUMMARY OF THE INVENTION

Preferred embodiments of the present invention address these and other needs by providing an electrochemical impedance spectroscopy enabled continuous glucose monitoring sensor system and method. This sensor system is arranged to utilize electrochemical impedance spectroscopy to monitor the condition of the sensor membranes of a subcutaneously insertable continuous monitoring sensor while being inserted, and then after insertion.

During the insertion process, the in vivo electrochemical impedance spectroscopy test results can be compared to a previously obtained reference test result to determine whether, for example, the sensor has been inserted properly, has been damaged or otherwise compromised, or is intact. Following acceptable readings of an intact sensor, further electrochemical impedance spectroscopy tests can ensue on the in vivo sensor. These tests can compare results to either an in vitro reference value, an in vivo reference value from previous studies, or to values obtained in vivo for the inserted sensor. Based on the results, an adjustment to a sensor calibration profile may ensue. For example, in the case of in vivo values taken for the inserted sensor, readings may be taken periodically, such as every 15 minutes. Subsequent readings can be compared to prior readings to identify whether the sensor membrane is intact, is becoming biologically fouled, is pistoning, or the like. These conditions can then be accounted for by adjusting a calibration profile of the sensor.

In accordance with one embodiment of the present invention, a method of testing the condition of a continuous analyte monitoring sensor in vivo comprises obtaining a reference parameter value for the continuous analyte sensor, inserting the continuous analyte sensor in vivo, performing electrochemical impedance spectroscopy on the in vivo sensor to obtain an in vivo parameter value, and comparing the in vivo parameter value to the reference parameter value to identify particular characteristics of the in vivo sensor.

The step of performing electrochemical impedance spectroscopy may be conducted during in vivo insertion and the reference parameter value and the in vivo parameter value may be capacitance values.

The step of performing electrochemical impedance spectroscopy may be conducted after in vivo insertion and the reference parameter value and the in vivo parameter value may be capacitance values. Based on the in vivo capacitance value, a sensor calibration profile of the in vivo sensor may be adjusted. The step of performing electrochemical impedance spectroscopy may be conducted periodically. The results of such periodic electrochemical impedance spectroscopy may also be utilized to adjust the sensor calibration profile. The adjustment may be based on a comparison of the in vivo capacitance value to the reference capacitance value.

The step of obtaining may be conducted after the step of inserting.

The reference parameter value may be an in vitro parameter value or an in vivo parameter value.

In accordance with another embodiment of the present invention, a method of testing a continuous glucose sensor in vivo may comprise obtaining a reference impedance value for the continuous glucose sensor, inserting the continuous glucose sensor in vivo, performing electrochemical impedance spectroscopy on the in vivo sensor to obtain an in vivo impedance value, comparing the in vivo impedance value to the reference impedance value to test the condition of the continuous glucose sensor.

The method may further comprise performing electrochemical impedance spectroscopy on the in vivo sensor to obtain a first in vivo capacitance value and performing electrochemical impedance spectroscopy on the in vivo sensor to obtain a second in vivo capacitance value, and comparing the second in vivo capacitance value to the first in vivo capacitance value to adjust a calibration profile of the continuous glucose sensor in vivo. The first in vivo capacitance value and the second in vivo capacitance value may be obtained at approximately 100 KHz.

BRIEF DESCRIPTION OF THE DRAWINGS

The subject matter regarded as the invention is particularly pointed out and distinctly claimed in the concluding portion of the specification. The invention, however, both as to organization and method of operation, together with the features, objects, and advantages thereof, may best be understood by reference to the following detailed description when read with the accompanying drawings in which:

FIG. 5 depicts a more detailed view of a continuous glucose monitoring sensor of the type described with respect to FIG. 2.

DETAILED DESCRIPTION

Figure 1:
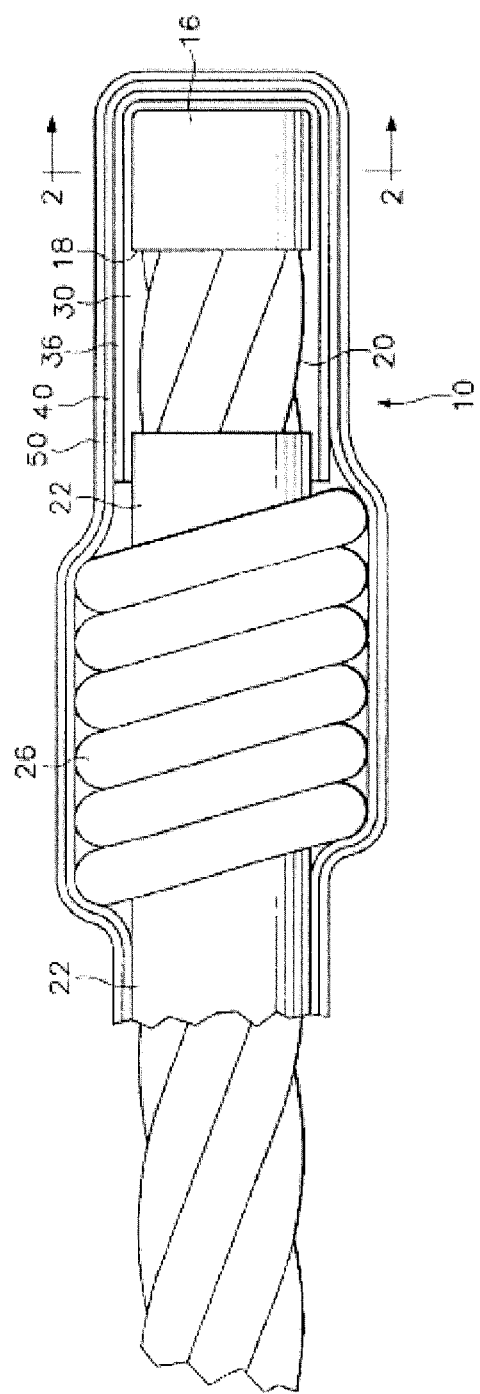
FIG. 1 depicts a diagrammatic view of a conventional continuous glucose monitoring sensor.

Certain preferred embodiments of the electrochemical impedance spectroscopy enabled continuous glucose monitoring sensor system and method are disclosed below in accordance with the present invention.

As discussed above, it is presently difficult to assess sensor viability of a CGM or other sensor types after insertion in the human body. This is generally caused by at least three issues, including damage to the sensor membrane during insertion, adverse biological reactions on the sensor within the body, and pistoning (movement) of the sensor in vivo. The present invention provides an electrochemical impedance spectroscopy enabled continuous monitoring sensor system and method to monitor viability and effectively evaluate and correct any disturbances in sensor accuracy, particularly for CGM sensor systems. Specifically, electrochemical impedance spectroscopy (EIS) is able to detect changes to the glucose sensor's accuracy as they occur, and thereby either warn the user of such changes or adjust the calibration of the sensor accordingly.

Preferred embodiments of the present invention address these and other needs by providing an electrochemical impedance spectroscopy enabled continuous glucose monitoring sensor system and method. This sensor system is arranged to utilize electrochemical impedance spectroscopy to monitor the condition of the sensor membranes of a subcutaneously insertable continuous monitoring sensor while being inserted, and then after insertion.

As stated previously, during the insertion process, the in vivo electrochemical impedance spectroscopy test results can be compared to a previously obtained reference test result to determine whether, for example, the sensor has been inserted properly, has been damaged or otherwise compromised, or is intact. Following acceptable readings of an intact sensor, further electrochemical impedance spectroscopy tests can ensue on the in vivo sensor. These tests can compare results to either an in vitro reference value, an in vivo reference value from previous studies, or to values obtained in vivo for the inserted sensor. Based on the results, an adjustment to a sensor calibration profile may ensue. For example, in the case of in vivo values taken for the inserted sensor, readings may be taken periodically, such as every 15 minutes. Subsequent readings can be compared to prior readings to identify whether the sensor membrane is intact, is becoming biologically fouled, is pistoning, or the like. These conditions can then be accounted for by adjusting a calibration profile of the sensor.

Conventional in vivo CGM sensors may be configured in a similar manner to the teachings of U.S. Pat. No. 6,613,379 issued to Ward, et al. (hereinafter "Ward"), the disclosure of which is hereby incorporated by reference as if fully set forth herein. As discussed in Ward, "continuous in vivo monitoring is done with a sensor that produces an electrical current that is proportional to the blood or subcutaneous tissue glucose level . . . by creating a reaction between immobilized glucose oxidase mixed with Bovine or Human Serum Albumin and glucose, to form gluconic acid and hydrogen peroxide. The hydrogen peroxide is oxidized at [a] platinum-indicating electrode 20 or anode surface, thereby freeing electrons that create a current and flow into the node." (Ward, col. 1 11.30-38.) The current may then be read to indicate glucose level.

In this regard, the sensor is equipped to convert an enzyme, or biological recognition element, to a detectable molecule. Typically, the enzyme will be glucose oxidase, the sensor will be a glucose monitoring sensor, and the detectable molecule will be hydrogen peroxide.

A conventional sensor taught by Ward is shown in FIG. 1 and comprises a set of fine wires acting as an indicating electrode or anode 20 positioned together with a dielectric material 22, 16 covering a substantial portion of the wires while defining an opening filled with various layered membrane materials 36, 40, 50. In one portion of the device, wound between the dielectric material 22 and the layered materials 36, 40, 50, is a cathode reference electrode 26. As such, the electrodes are all embedded within the layered membrane materials 36, 40, 50.

The layered materials include an optional extreme outer layer of material designed to encourage the growth of neovascularized tissue, referred to herein as a growth layer 50. To encourage growth of neovascularized tissue, the growth layer should have finely spaced apertures with a typical diameter of about 5 μm. A number of materials are available for this function, with a commonly available membrane being expanded poly tetrafluoroethylene.

Beneath the growth layer 50, if so provided, or as an extreme outer layer if not, is a permeable membrane layer 40. The permeable membrane 40 may be comprised of a barrier breathing film, an amphiphobic polyurethane material.

An inner layer 36 is formed from glucose oxidase mixed with bovine or human serum albumin and glutaraldahyde. It is this glucose oxidase layer 36 that reacts with in vivo glucose to provide electrons at the surface of the indicating electrode 20. The flow of electrons is then measured against a calibration process to determine the level of glucose in vivo.

It is well known that impedance is the opposition to flow of alternating current. Since the 1970's, EIS has been used as a tool to analyze difficult and complicated systems by measuring impedance of a system over a range of frequencies. The results, including all of the parameters utilized, can be plotted in both Bode and Nyquist plots.

CGM sensors of the type disclosed above are physiochemical systems that possess energy storage and dissipation properties that may be examined by EIS. For example, the impedances, resistance, and capacitance at all frequencies of the electrode sensor may be examined. Generally, their respective values should remain constant outside changes in the experimental conditions or changes in the characteristics of the membranes 50, 40, 36. By keeping the experimental conditions constant, changes in the membranes 50, 40, 36 may be revealed. Those changes may simply be identified, or may be compensated for by adjusting the sensor's calibration profile.

Figure 2:
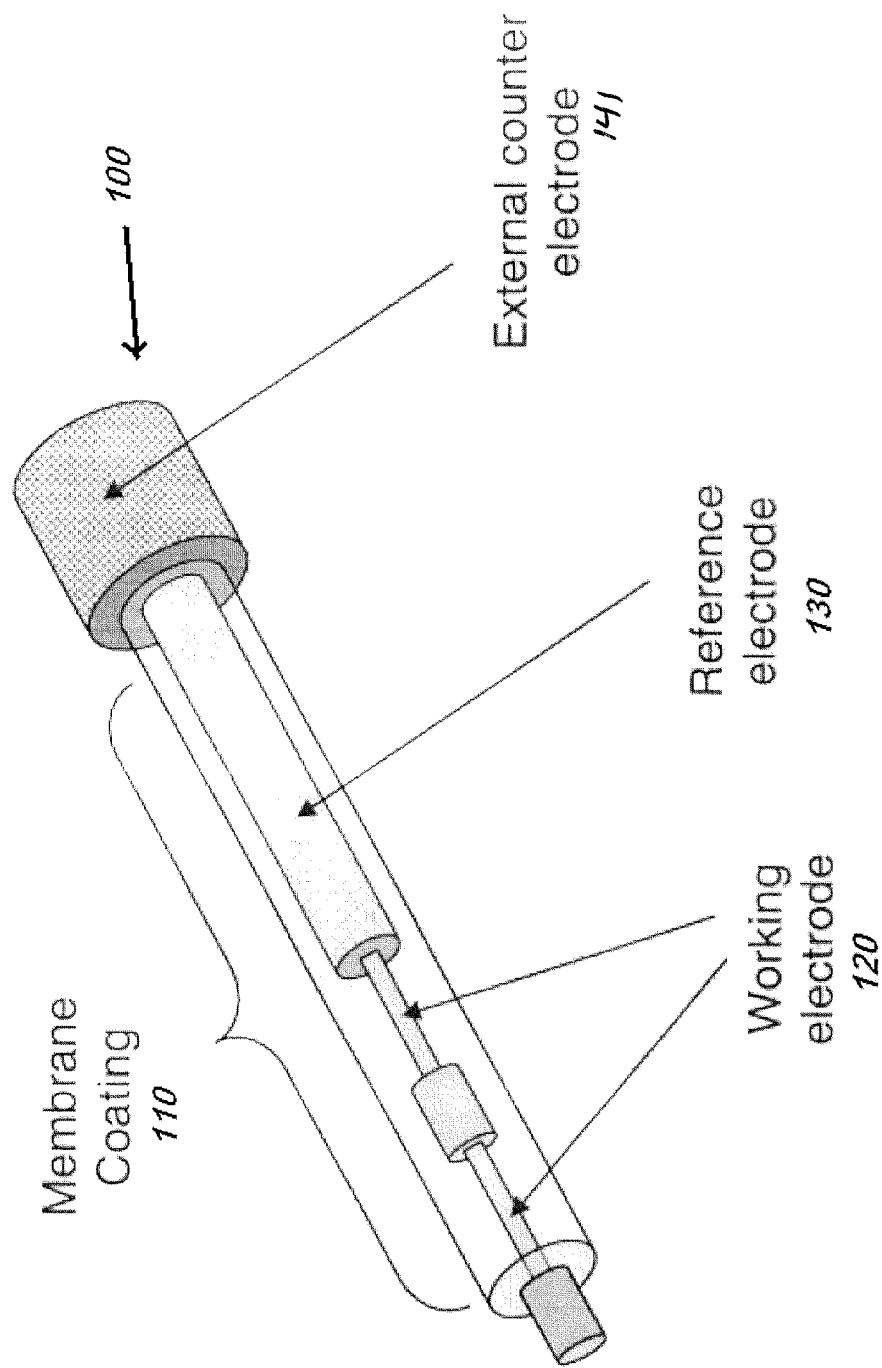
FIG. 2 depicts a diagrammatic view of a continuous glucose monitoring sensor in accordance with certain aspects of the present invention.

In order to optimally perform EIS on a CGM, changes from the conventional CGM may be employed. Depicted as FIG. 2 is an in vivo sensor for an EIS enabled continuous glucose monitoring sensor system and method in accordance with certain preferred aspects of the present invention. Although the EIS enabled CGM sensor is shown as cylindrical, it will be appreciated that the shape is somewhat irrelevant. For operation, the EIS enabled CGM sensor requires an electrode and surrounding membrane, and may be relatively flat, a solid bounded by equal (e.g. cube) or unequal sides, or other geometric and non-geometric configurations. As shown in FIG. 2, the sensor 100 includes a membrane coating 110 surrounding a working electrode 120 and reference electrode 130 configured in much the same manner as the Ward sensor discussed with respect to FIG. 1, which is considered a 2-electrode design. In order to utilize EIS to detect membrane integrity, the sensor 100 is also equipped with an external counter electrode 141 external to the membrane coating 110.

Another continuous glucose monitoring sensor of the type described with respect to FIG. 2 is shown in FIG. 5. As depicted in FIG. 5, the sensor 100 includes a membrane coating 110 surrounding a working electrode 120 and a reference electrode 130. The sensor is also equipped with a counter electrode 141 external to the membrane coating 110.

As before, the membrane coating may include an optional outer layer 150. Beneath outer layer 150, or as the extreme outer layer if layer 150 is not provided, is a permeable membrane layer 140. An inner layer 136, below the permeable membrane layer 140, is formed from glucose oxidase mixed with bovine or human serum albumin and glutaraldahyde. It is this glucose oxidase layer 136 that reacts with in vivo glucose to provide electrons at the surface of the indicating electrode 120. The flow of electrons is then measured against a calibration process to determine the level of glucose in vivo. Another layer in the form of an exclusion layer 138, may also be provided. If provided, this layer may exclude certain elements from passing. For example, acetaminophen exclusion layers are well known in the art.

Upon insertion of the sensor 100, the counter electrode 141 may either be inserted in vivo with the remainder of the sensor 100 including the working electrode 120 and reference electrode 130, or may remain outside the skin. In either configuration, intimate contact with the remaining portions of the sensor 100 is maintained. It is noted herein that at approximately 100 KHz, skin impedance is in the approximate range of 100-300 Ω, so it does not significantly affect the impedance value of the coating. Other frequencies generally between 0.001 Hz and 1,000,000 Hz may also be utilized. In addition, more than one frequency may be tested. If more than one frequency is utilized, it will be appreciated that the results from each frequency queried can be analyzed against each other to confirm the test results.

The EIS tests may be performed using specialized equipment presently devoted to such purposes, or may be performed using equipment introduced in an otherwise typically styled meter.

There are two parameters that may be extracted from the EIS measurement, R and C, preferably at 100 KHz. In order to obtain such values, the electronic component of the meter, or potentiostat, first applies a DC potential that does not incur any electrochemical reaction on the working electrode. In exemplary cases, the DC potential may range from 0 V to 0.3 V vs. an AgCl reference electrode. With this DC potential, a small AC signal (1 to 10 mV) is added to the working electrode at a certain frequency, for example the preferred 100 KHz. The results may then be directly presented in a time domain as signal amplitude vs. time. After conducting a Fourier transform, this data can be converted to frequency domain as signal amplitude vs. frequency. Therefore, R and C and other values can be calculated at the frequency of interest.

Figure 3:
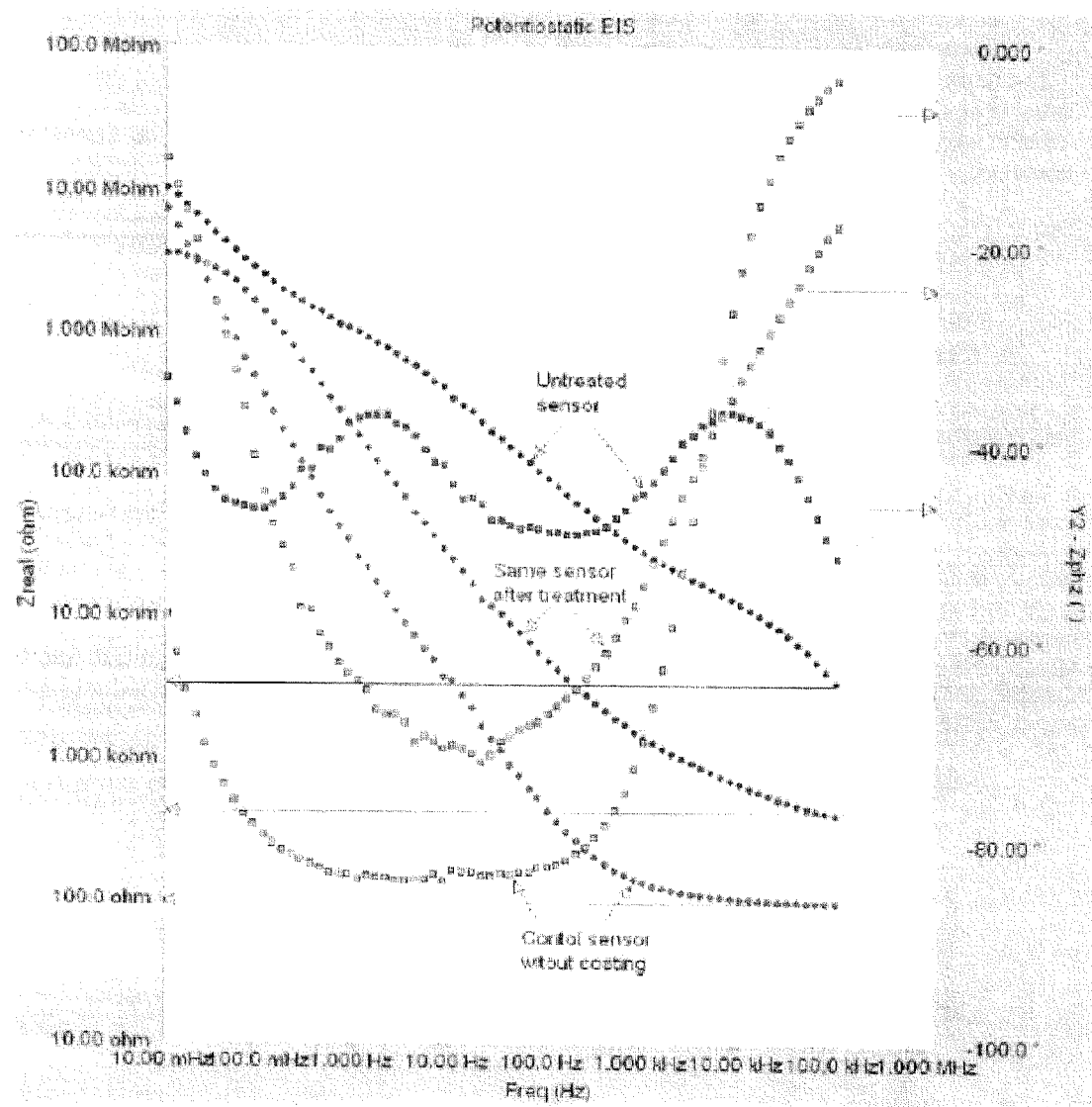
FIG. 3 depicts a Bode plot of test results for Test Sample 1, discussed herein.

In general, the use of impedance as a testing mechanism results in a Bode plot, such as the Bode plot shown in FIG. 3. To arrive at the particular plot shown in FIG. 3, and specifically for a Test Example 1, Applicant (1) initially tested the EIS sensors, (2) intentionally treated the pre-tested sensors to simulate in vivo insertion action, and (3) conducted a second round of EIS testing on the treated sensors. In the field, and in practice, step (2) is replaced with actual in vivo insertion. The EIS test results from Test Example 1 are shown in FIG. 3.

One of the significant differences among the EIS data for the three sensor conditions is the phase shift at the intermediate frequency region (1 Hz to 100 Hz) on the Bode plot. The phase shift can be read at the right Y-axis of the Bode plot shown in FIG. 3. The control sensor shows the smallest phase shift ~45° because it has an almost perfect coating and there is no exposed area. The treated sensor phase shift is ~70°, in between the undamaged value (~45° and the control value (~80°. This result indicates that the coating is not as intact as the undamaged sensor, and there is some area of the sensor electrode exposed directly to the solution because of damage.

One may again consider R and C at 100 KHz, which are the total resistance and capacitance at high frequency. Both R and C can be obtained from either Bode or Nyquist plots (R is shown in FIG. 3, C is not shown herein). Normally, the impedance at high frequency is equal to the solution resistance ($R_s$) plus the electrode impedance minus the organic coating resistance ($R_e$) and double-layer capacitance on the electrode ($C_e$).

When there is no coating on the electrode, the impedance at 100 KHz is equal to the solution resistance, which is 98Ω for Test Example 1.

If one only looks at the capacitance portion, the capacitance of the double-layer on the electrode is 890.4 pF. The test sensors normally have a near-perfect coating. That means total impedance contributed from the resistance of the coating is high, but contribution from the double-layer capacitance is low since there is almost no direct exposure of the electrode.

In Test Example 1, total R is 3448Ω and C is 225.2 pF. After the treatment, the high resistance coating has been disrupted, so the R drops significantly to 410Ω. Because of that disruption, a large area of the electrode is in direct contact with electrolyte, and the contribution from the double-layer capacitance is significantly increased to 1123 pF. Table 1 depicts these values.

| SENSOR | R at 100 KHz (Ω) | C at 100 KHz (pF) |
|---|---|---|
| Untreated Sensor | 3448 | 225.2 |
| Treated Sensor | 410 | 1123 |
| Control Sensor | 98 | 890.4 |

By evaluating the value of R and C at 100 KHz after insertion, one can determine whether the sensor coating has been disrupted or not.

Among the number of evaluation criteria, C at 100 KHz has been found to be the easiest and fastest to acquire, extract, and compare with. Tests have shown that it takes less than 1 second even when the data acquisition is repeated many times to average the resulting value. For example, the empirical value C at 100 KHz of undamaged sensors in 0.1 M pH7 PBS buffer virtually always tests lower than 300 pF. Any readings higher than 300 pF indicates that the sensor has been damaged to a certain extent. This number may vary in vivo, but can be measured and recorded for similar evaluation. This would enable use of the teachings herein for in vivo operations. Of course, it is to be understood that the in vivo results, as compared to the in vitro reference values, would depend on the physical condition of the in vitro sensor and the environmental conditions in which the in vitro reference values were obtained.

DURING INSERTION—Based on the foregoing, three EIS capacitance results could be expected during the in vivo insertion process, each explaining a possible scenario.

a. NO CAPACITANCE—If no value is returned, or if the value fluctuates between zero and a value reading, the sensor is likely not hydrated indicating that the sensor is not inserted in the liquid environment, such as interstitial fluid, cerebral fluid, blood, or the like. This may also indicate that at least the external counter electrode is not in contact with the skin.

b. LOWER OR EQUAL CAPACITANCE—If the value is lower or equal than the standard value (for example the 300 pF value identified above for Test Example 1), the sensor is likely inserted correctly.

c. HIGHER CAPACITANCE—If the value is higher than normal, the sensor membrane coating is likely damaged due to the insertion process or otherwise.

When there is no value returned, a warning may be given to the user to reinsert the sensor. When a higher than normal value is returned, a warning that the sensor performance may be affected due to questionable sensor integrity may be given. In such case, a user may replace the sensor immediately rather than wait the standard 15 minute to 3 hour run-in phase before being alerted to the fact that the sensor cannot be calibrated or has a shortened useful life.

POST INSERTION—After the insertion process, another four EIS results could be expected during the testing process. These scenarios are based on the comparison of capacitance values over time after the sensor is inserted. The four scenarios are detailed below:

a. NO CAPACITANCE—Capacitance drops to zero, when there is adverse sensor movement, such as pistoning movement causing the external counter electrode not to contact the skin, interstitial fluid, cerebral fluid, blood, etc. This may also be evidenced by an intermittent drop to zero due to repeated shifting from contact to non-contact.

b. CAPACITANCE LOWERS OVER TIME—Capacitance lowers when there is biofouling, where protein precipitates in or on the membrane over time.

c. CAPACITANCE REMAINS EQUAL OVER TIME—Capacitance remains the same when the sensor remains intact. This is the preferred scenario.

d. CAPACITANCE RAISES OVER TIME—Capacitance raises when the sensor membrane coating is eroded, damaged, or abused over time.

Following any of these four scenarios, the user may be alerted to the result, such as by warning the user to replace the sensor. Alternatively, and in preferred embodiments, the sensor system may utilize the results to adjust a calibration profile of the sensor.

Studies in this area have been performed, for example those described in *Foreign Body Response Investigated With an Implanted Biosensor by In Situ Electrical Impedance Spectroscopy*, published by Floyd B. Karp, Neil A. Bernotski, Thelma I. Valdes, Karl F. Böhringer, and Buddy D. Ratner, in the IEEE Sensors Journal, Vol. 8, No. 1, Jan. 2008. Using an in vivo calibration adjustment procedure permits a user to minimize the number of finger pricks required for calibration, as calibration is instead performed through non-invasive EIS.

Figure 4:
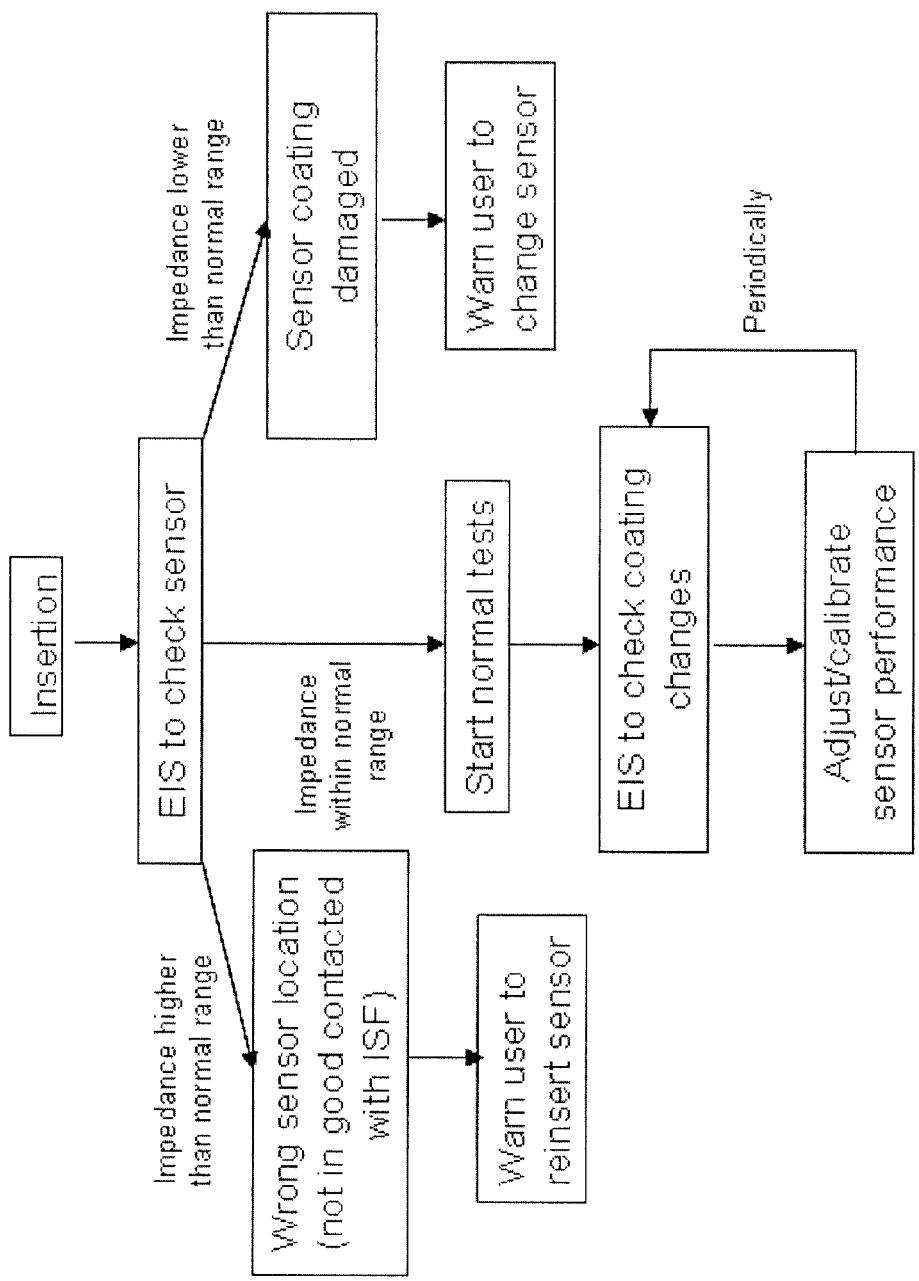
FIG. 4 depicts a flow chart indicating one method of using electrochemical impedance spectroscopy with a continuous glucose meter in accordance with the present invention.

FIG. 4 depicts a flow chart indicating how EIS may work with a sensor system. After insertion of the sensor in vivo, EIS is initiated to make certain that the sensor is located properly and there is no damage to the sensor. Once an EIS result indicates that capacitance value is acceptable, the normal measurement starts. During the test, EIS runs periodically, on the order of every 5 minutes to 15 minutes, or longer. These frequencies offer many more calibration data points than present techniques, which may only be completed on the order of every 12 hours. Such tests monitor the sensor coating changes and either adjust the sensor performance according to the EIS results (calibration), or in the case of pistoning detection warn the users that the sensor may need reinsertion or replacement.

Although the disclosure heretofore discloses use of R and C at 100 KHz values, there are other parameters and other frequencies that could possibly be used to evaluate membrane integrity depending on the application. Such parameters have complete viability. For Test Example 1, R and C at 100 KHz were specifically chosen in vitro, because they show significant differences between intact and damaged membranes. For other applications, R and C at 100 KHz might not be the preferred test parameters as they may not provide enough fluctuation to differentiate membrane changes, whereas other parameters at other frequencies may. The preferred parameters may change depending on the configuration of the sensor and the enzyme tested for. Other parameters that may be utilized in this regard, include, but are not limited to:

Frequency: the frequency ranged can be chosen from 0.001 Hz to 1,000,000 Hz. All the parameters (such as R and C) can be evaluated at a single frequency point, multiple frequency points, or a pattern from a frequency range.

Parameters: the following parameters can be calculated from impedance data:

$R$, $Z_{imag}$, $Z_{mod}$, $Z_{phz}$—Calculated value of impedance
$Y_{real}$, $Y_{imag}$—Admittance (calculated from Z)
C—Calculated value of capacitance
$I_{dc}$, $V_{dc}$—DC component of current and voltage All such parameters may be evaluated in certain manners when combined with the frequencies identified above. Such manners include (a) an evaluation of the change of one parameter (such as percentage change), (b) an evaluation of the change of multiple parameters, or (c) an evaluation of the relationship of multiple parameters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A method of testing the condition of a continuous analyte monitoring sensor in vivo comprising:
   obtaining a reference capacitance value for the continuous analyte sensor;
   inserting the continuous analyte sensor in vivo;
   performing electrochemical impedance spectroscopy on the in vivo sensor to obtain an in vivo capacitance value; and
   comparing, by electrochemical impedance equipment, the in vivo capacitance value to the reference capacitance value to identify particular characteristics of the in vivo sensor, wherein the step of performing electrochemical impedance spectroscopy is conducted during in vivo insertion.

2. The method of claim 1, wherein the sensor further comprises an external counter electrode, wherein when the in vivo capacitance value is zero or intermittently zero during insertion, the sensor is not in sufficient contact with interstitial fluid or the external counter electrode is not in contact with a skin of a user.

3. The method of claim 2, further comprising warning the user to reinsert the sensor.

4. The method of claim 1, wherein when the in vivo capacitance value is greater than the reference capacitance value during insertion, the sensor coating is damaged, and a warning to the user to replace the sensor is provided.

5. The method of claim 1, wherein the step of obtaining the reference capacitance value is conducted after the step of inserting.

6. The method of claim 1, wherein the step of comparing is conducted by a Bode plot to identify phase shifts.

7. The method of claim 1, wherein the sensor further comprises a working electrode within a sensor membrane and a membrane layer overlies an outer surface of the sensor membrane.

8. The method of claim 7, wherein the comparing step identifies whether the sensor is in a proper position and whether the membrane layer is damaged.

9. The method of claim 1, further comprising determining whether the in vivo capacitance value is equal to, less than, or greater than the reference capacitance value during insertion to identify the particular characteristic of the sensor.

10. The method of claim 9, further comprising an external electrode, wherein when the in vivo capacitance value is zero or intermittently zero during insertion, the sensor is identified as being in an improper position.

11. The method of claim 9, wherein when the in vivo capacitance value is greater than the reference capacitance value during insertion, the sensor coating is identified as being damaged.

12. The method of claim 9, wherein when the in vivo capacitance value is less than the reference capacitance value during insertion, the sensor coating is identified as being intact.

13. The method of claim 1, wherein the in vivo capacitance value is a first in vivo capacitance value, the method further comprising:
   performing electrochemical impedance spectroscopy on the in vivo sensor to obtain a second in vivo capacitance value, and
   comparing the second in vivo capacitance value to the first in vivo capacitance value to adjust a calibration profile of the continuous glucose sensor in vivo.

14. A method of testing the condition of a continuous analyte monitoring sensor in vivo comprising:
   obtaining a reference impedance value for the continuous analyte sensor;
   inserting the continuous analyte sensor in vivo;
   performing electrochemical impedance spectroscopy on the in vivo sensor to obtain an in vivo impedance value; and
   comparing, by electrochemical impedance equipment, the in vivo impedance value to the reference impedance value to identify particular characteristics of the in vivo sensor, wherein the step of performing electrochemical impedance spectroscopy is conducted during in vivo insertion.

15. The method of claim 14, wherein the sensor further comprises a working electrode within a sensor membrane and a membrane layer overlies an outer surface of the sensor membrane, and wherein the comparing step identifies whether the sensor is in a proper position or whether the membrane layer is damaged.

16. The method of claim 14, wherein the sensor further comprises an external counter electrode.

17. The method of claim 14, wherein the step of comparing is further conducted by using a Bode plot to identify phase shifts.

* * * * *

UNITED STATES PATENT AND TRADEMARK OFFICE
CERTIFICATE OF CORRECTION

PATENT NO. : 8,868,151 B2
APPLICATION NO. : 12/857116
DATED : October 21, 2014
INVENTOR(S) : Stanley A. Telson et al.

Page 1 of 1

It is certified that error appears in the above-identified patent and that said Letters Patent is hereby corrected as shown below:

IN THE SPECIFICATION

In Column 1, Line 54, delete "often as" and insert -- often as 10 --, therefor.
In Column 5, Line 14, delete "glutaraldahyde." and insert -- glutaraldehyde. --, therefor.
In Column 5, Line 65, delete "glutaraldahyde." and insert -- glutaraldehyde. --, therefor.

Signed and Sealed this
Fourteenth Day of April, 2015

Michelle K. Lee
*Director of the United States Patent and Trademark Office*

UNITED STATES PATENT AND TRADEMARK OFFICE
CERTIFICATE OF CORRECTION

Page 1 of 1

PATENT NO.      : 8,868,151 B2
APPLICATION NO. : 12/857116
DATED           : October 21, 2014
INVENTOR(S)     : Stanley A. Telson et al.

It is certified that error appears in the above-identified patent and that said Letters Patent is hereby corrected as shown below:

On the Title Page, item (75), under "Inventors", in Column 1, Line 2, delete "Cortland Manor," and insert -- Cortlandt Manor, --, therefor.

IN THE SPECIFICATION

In Column 1, Line 54, delete "often as" and insert -- often as 10 --, therefor.
In Column 5, Line 14, delete "glutaraldahyde," and insert -- glutaraldehyde. --, therefor.
In Column 5, Line 65, delete "glutaraldahyde." and insert -- glutaraldehyde. --, therefor.

This certificate supersedes the Certificate of Correction issued April 14, 2015.

Signed and Sealed this
Sixteenth Day of June, 2015

Michelle K. Lee
*Director of the United States Patent and Trademark Office*